(12) United States Patent
Logan

(10) Patent No.: US 9,750,632 B1
(45) Date of Patent: Sep. 5, 2017

(54) LOWER BACK SUPPORT SYSTEM

(71) Applicant: Charles P. Logan, Tujunga, CA (US)

(72) Inventor: Charles P. Logan, Tujunga, CA (US)

(*) Notice: Subject to any disclaimer, the term of this patent is extended or adjusted under 35 U.S.C. 154(b) by 55 days.

(21) Appl. No.: 13/948,918

(22) Filed: Jul. 23, 2013

(51) Int. Cl.
 *A61F 5/02* (2006.01)
(52) U.S. Cl.
 CPC .................................. *A61F 5/028* (2013.01)
(58) Field of Classification Search
 CPC .... A61F 5/028; A61F 5/02; A61F 5/03; A61F 5/026
 USPC .......................................................... 602/19
 See application file for complete search history.

(56) References Cited

U.S. PATENT DOCUMENTS

| | | | |
|---|---|---|---|
| 1,776,864 A | 9/1930 | Cameron | |
| 2,282,021 A | 5/1942 | Benningfield | |
| 3,101,718 A | 8/1963 | Rocker | |
| 3,603,316 A | 9/1971 | Lehman | |
| D235,788 S | 7/1975 | Eberhardt | |
| 3,927,665 A | 12/1975 | Wax | |
| 4,022,197 A | 5/1977 | Castiglia | |
| 4,475,543 A | 10/1984 | Brooks et al. | |
| 4,541,152 A | 9/1985 | DiMarco et al. | |
| 4,545,370 A | 10/1985 | Welsh | |
| 4,833,730 A | 5/1989 | Nelson | |
| 4,836,194 A | 6/1989 | Sebastian et al. | |
| 5,040,524 A | 8/1991 | Votel et al. | |
| 5,123,147 A * | 6/1992 | Blair .................. A44B 11/2526 24/633 |
| 5,176,131 A | 1/1993 | Votel et al. | |
| 5,188,586 A | 2/1993 | Castel et al. | |
| D352,114 S | 11/1994 | Nicholson | |
| 5,363,863 A * | 11/1994 | Lelli ........................ A61F 5/028 128/876 |
| 5,388,274 A | 2/1995 | Glover et al. | |
| 5,690,609 A * | 11/1997 | Heinze, III ..................... 602/19 |
| 5,954,250 A * | 9/1999 | Hall ......................... A45F 3/047 224/262 |
| 5,954,253 A * | 9/1999 | Swetish ..................... A45F 3/08 224/628 |
| D422,709 S | 4/2000 | Caswell | |
| 6,099,490 A * | 8/2000 | Turtzo ..................... A61F 5/028 2/311 |
| 6,896,662 B2 * | 5/2005 | Heffez .................... A61F 5/028 602/19 |
| 2010/0125983 A1* | 5/2010 | Keene et al. ................. 24/593.1 |
| 2010/0204630 A1* | 8/2010 | Sandifer et al. ................ 602/19 |

(Continued)

*Primary Examiner* — Ophelia A Hawthorne

(57) ABSTRACT

A lower back support system (LBSS) that provides increased support to a person's lower spine and back muscle group. The LBSS includes a first belt, a second belt, a quick release buckle and an adjustable belt glide. Additionally, a back rack that consists of a first shoulder support, a second shoulder support as well as other yoke, front and side supports can also be utilized. Substantially centered and attached by an attachment device to the front of the first belt is an abdominal support brace. Substantially centered and attached to the rear of the first belt is a back support brace which is specially designed and dimensioned to provide maximum support to a typical person's lower back. When wearing the LBSS a person is more protected against strain and injury by supporting his/her lower back when lifting, carrying or wearing an object(s) or being physically jarred. The LBSS shifts load from a person's single spine to their two legs.

4 Claims, 13 Drawing Sheets

(56) References Cited

U.S. PATENT DOCUMENTS

2011/0140405 A1\* 6/2011 Wiseman et al. ............. 280/807
2011/0203531 A1\* 8/2011 Spinelli ........................ 119/770

\* cited by examiner

LOWER BACK SUPPORT SYSTEM

TECHNICAL FIELD

The invention generally pertains to human body support devices, and more particularly to an integrated system that provides significantly increased support to a person's lower back region.

BACKGROUND ART

Lower back pain (LBP) is one of humanity's most frequent complaints. In the U. S., acute lower back pain (also called lumbago) is the fifth most common reason for physician visits, and the lower back is the most common site of back injuries. About eight out of ten adults experience back pain at some point in their life, and five out of ten working adults have back pain every year. According to the U.S. National Library of Medicine, at any given point in time, at least 15% of individuals report that they are experiencing LBP. Worldwide 1 billion people are experiencing lower back pain right this minute.

Back pain usually originates from the muscles, nerves, bones, joints or other structures in the spine. The spine is a complex interconnecting network of nerves, joints, muscles, tendons and ligaments, all of which are capable of producing pain. Large nerves that originate in the spine and go to the legs and arms can make pain radiate to the extremities.

Back pain may have a sudden onset or can be a chronic pain; it can be constant or intermittent, stay in one place or radiate to other areas. It may be a dull ache, or a sharp, piercing or burning sensation. The pain may radiate into the brain, arms and hands as well as the legs or feet, and may include symptoms other than pain. These symptoms may include tingling, dizziness, weakness or numbness.

There have been many attempts of finding a way to end or alleviate back pain, especially lower pain back which is especially common. Some of the solutions to the back pain problem include certain exercises and stretching actions, belts or other devices that are worn, and medicinal pain killers which can often mask the pain for a while but do not address the cause of the pain.

Of all the solutions, one of the most promising was a specially-designed belt that when worn would reduce the pain. There have been many types of belts, and other worn devices, which have been made available. The functionality and actual effectiveness of the various belts and/or devices has varied—some designs have proven to be better than others. Unfortunately, no belt or belt combination design has adequately addressed the fundamental causes of lower back pain. What is needed is a belt or belt and device combination that is designed based upon actual physiology and knowledge of the causes of back pain. A belt that is designed in this manner would be able to effectively reduce injuries and the back pain that is regularly experienced.

A search of the prior art did not disclose any literature or patents that read directly on the claims of the instant invention. However, the following U.S. Patents are considered related.

| PAT. NO. | INVENTOR | ISSUED |
|---|---|---|
| D235,788 | Eberhardt | 8 Jul. 1975 |
| D352,114 | Nicholson | 1 Nov. 1994 |
| D422,709 | Caswell | 11 Apr. 2000 |
| 1,776,864 | Cameron | 30 Sep. 1930 |
| 2,282,021 | Berunngfield | 5 May 1942 |
| 3,101,718 | Rocker | 27 Aug. 1963 |
| 3,603,316 | Lehman | 7 Sep. 1971 |
| 3,927,665 | Wax | 23 Dec. 1975 |
| 4,022,197 | Castiglia | 10 May 1977 |
| 4,475,543 | Brooks et al | 9 Oct. 1984 |
| 4,541,152 | DiMarco et al | 17 Sep. 1985 |
| 4,545,370 | Welsh | 8 Oct. 1985 |
| 4,833,730 | Nelson | 30 May 1989 |
| 4,836,194 | Sebastian et al | 6 Jun. 1989 |
| 5,040,524 | Votel et al | 20 Aug. 1991 |
| 5,176,131 | Votel et al | 5 Jan. 1993 |
| 5,188,586 | Castel et al | 23 Feb. 1993 |
| 5,363,863 | Lelli et al | 15 Nov. 1994 |
| 5,388,274 | Glover et al | 14 Feb. 1995 |

DISCLOSURE OF THE INVENTION

In its basic design, the lower back support system (LBSS) is comprised of a first belt, a second belt, a quick release adjustable buckle, an adjustable belt glide, an abdominal support brace, a back support brace, a first shoulder support and a second shoulder support. The adjustable buckle and the adjustable belt glide allow the first belt and the second belt to be securely maintained around a person's waist at a selective tightness. Substantially centered and attached by an attachment means to the front of the first belt is the abdominal support brace which is contoured to a person's abdominal area, and substantially centered and attached by an attachment means to the rear of the first belt is the back support brace, which is contoured to a person's lower back. Extending upward along a person's back from the second belt and continuing over the right shoulder is the first shoulder support, and extending from the second belt upward along a person's back and over the left shoulder is the second shoulder support. Both shoulder supports are attached b an attachment means to the second belt, the attachment means is designed to allow the shoulder supports, as well as any object that is being carried on the shoulder supports, to pivot horizontally side-to-side which provides greater comfort and balance, when leaning left or right, twisting, squatting, or walking (or running) when carrying an object. The second ends of both shoulder support terminate at a location on a person's upper chest. When wearing the LBSS, the combined use of the belt with the abdominal support brace and the back support brace, along with the shoulder supports, supports the spine against the strain a person experiences when lifting, and along with the shoulder supports, will shift the weight of a load on a person's shoulders and spine to their hips and legs, thereby reducing the strain on the spine when carrying or wearing an object(s) (such as a backpack).

In view of the above disclosure, the primary object of the invention is to provide a lower back support system that increases support to a person's lower spine/muscle groups particularly when jolted or lifting, and takes the load off the spine when carrying or wearing an object(s).

In addition to the primary object, it is also an object of the invention to provide a lower back support system that:
is easy to assemble and put on,
is light weight and comfortable to wear,
offers solid support (not elastic) to the lower back,
can be made in various sizes for children and adults, men and women of all shapes, instantly adjusts to six waist sizes to increase or decrease back support, is effective in areas of sports, lower back health, industry, freight handling and the trades, is especially effective when used by soldiers who are carrying/wearing heavy loads for long distances, shifts the weight of a load from a person's single spine to their two legs, is also effective for campers/hikers, mothers carrying babies, children carrying book bags, rescue workers, firemen, police, or anyone wearing or carrying a load, is easily cleaned and stored when not in use, is robust and long lasting, can be quickly and easily put-on by a single person, in case of an emergency the attachment buckle can be instantly released by one hand, can be sold as a combination product with backpacks of all sizes, or just as a support system to be used with or without a person's existing backpack (or other objects (s)), can include a bracket or hook that is attached to either or both shoulder supports or belt for supporting a load, is cost effective from both a manufacturer's and a consumer's point of view as it is made with common production methods and materials.

These and other objects and advantages of the present invention will become apparent from the sub sequent detailed description of the preferred embodiment and the appended claims taken in conjunction with the accompanying drawings.

BEST MODE FOR CARRYING OUT THE INVENTION

Figure 1:
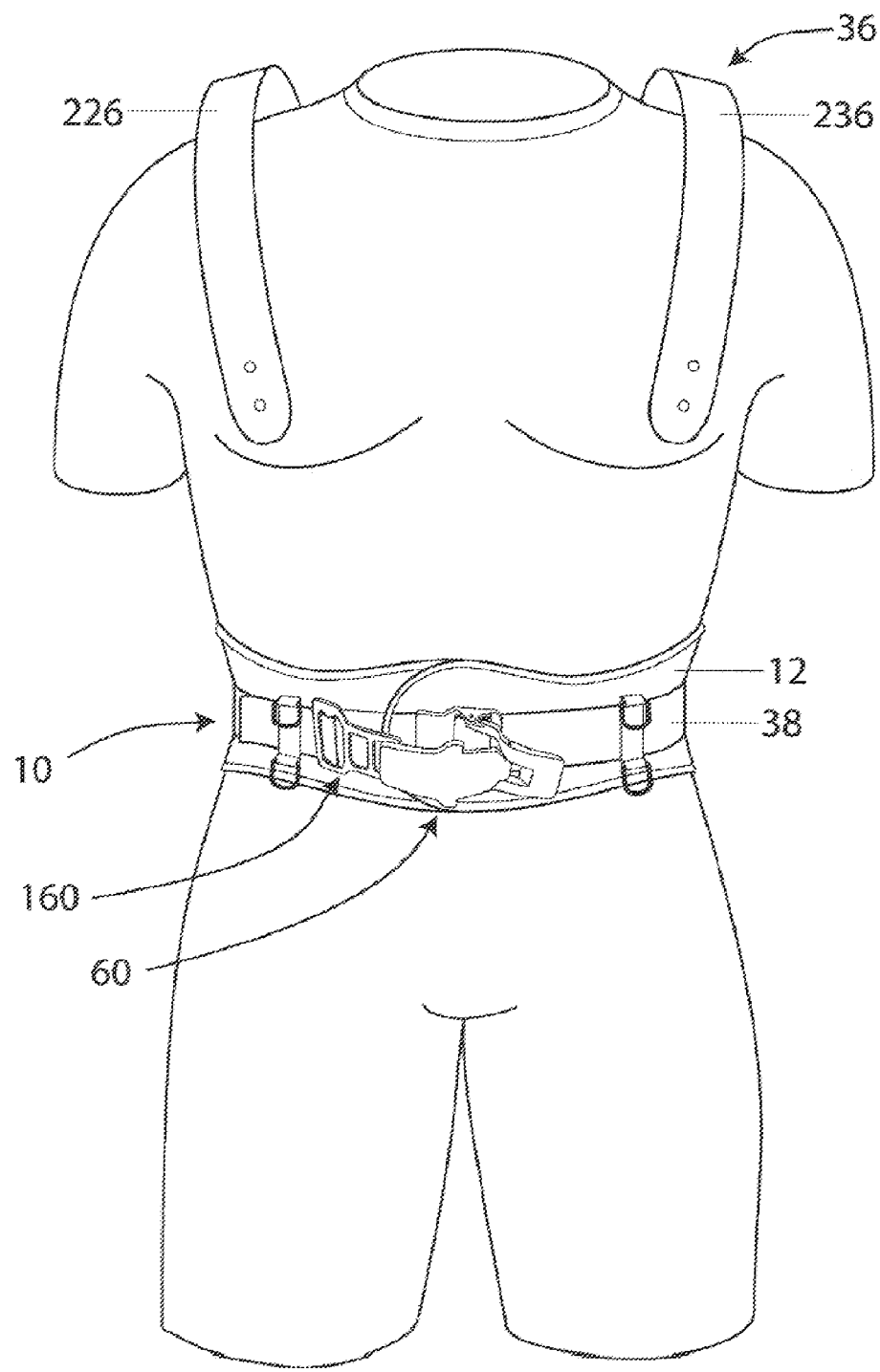
FIG. 1 is a front elevational view of the lower back support system shown worn by a person.

The best mode for carrying out the invention is presented in terms that disclose a preferred embodiment of a lower back support system (LBSS). Back pain or injury is one of the most prevalent problems experienced by people throughout the world. There are multiple causes of, or reasons for, back pain or injury. But one of the most common is over-exertion as a result of lifting, carrying or wearing an object(s). Back pain, and in particular lower back pain, can vary from a slight occasional pain to a completely debilitating, constant pain that severely compromises a person's ability to perform or participate in routine activities.

The instant LBSS can alleviate a significant amount of lower back pain or injury which is caused by lifting, carrying or wearing an object(s), such as a backpack. The benefits afforded by the LBSS are applicable to many people. For example, students who must carry multiple heavy books as well as supplies in a backpack, mothers carrying baby carriers, hikers and other outdoor-enthusiasts who carry camping supplies on their back, and soldiers who are typically required to wear a backpack that can weigh up to 150 pounds.

As shown in FIGS. 1-13, the LBSS 10 is comprised of the following major elements: a first belt 12, a second belt 38, a buckle 60, an adjustable belt glide 160, an abdominal support brace 190, a back support brace 206, a first shoulder support 226, a second shoulder support 236, and back rack 36.

Figure 2:
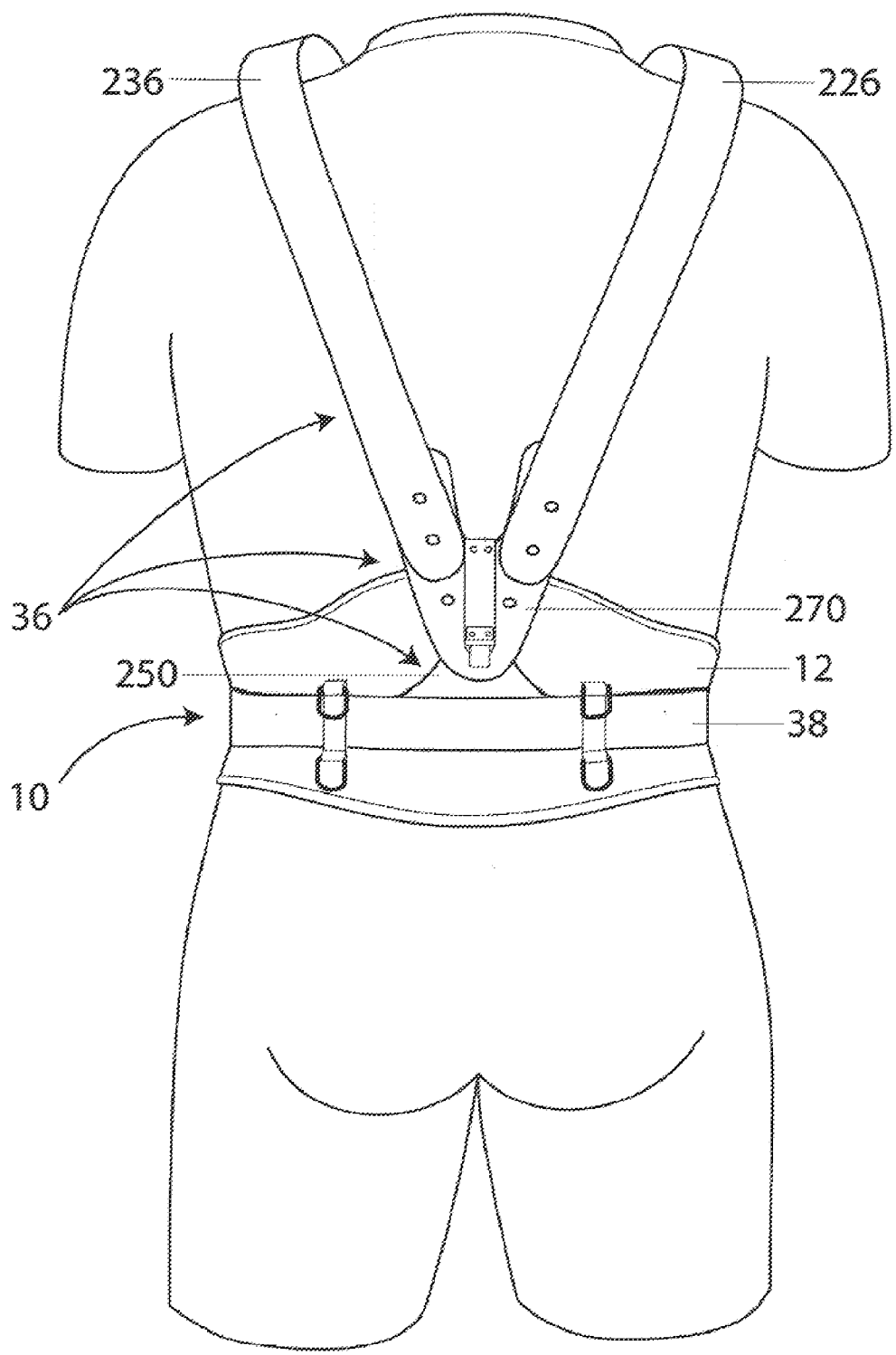
FIG. 2 is a rear elevational view of the lower back support system and back rack shown worn by a person.
Figure 3:
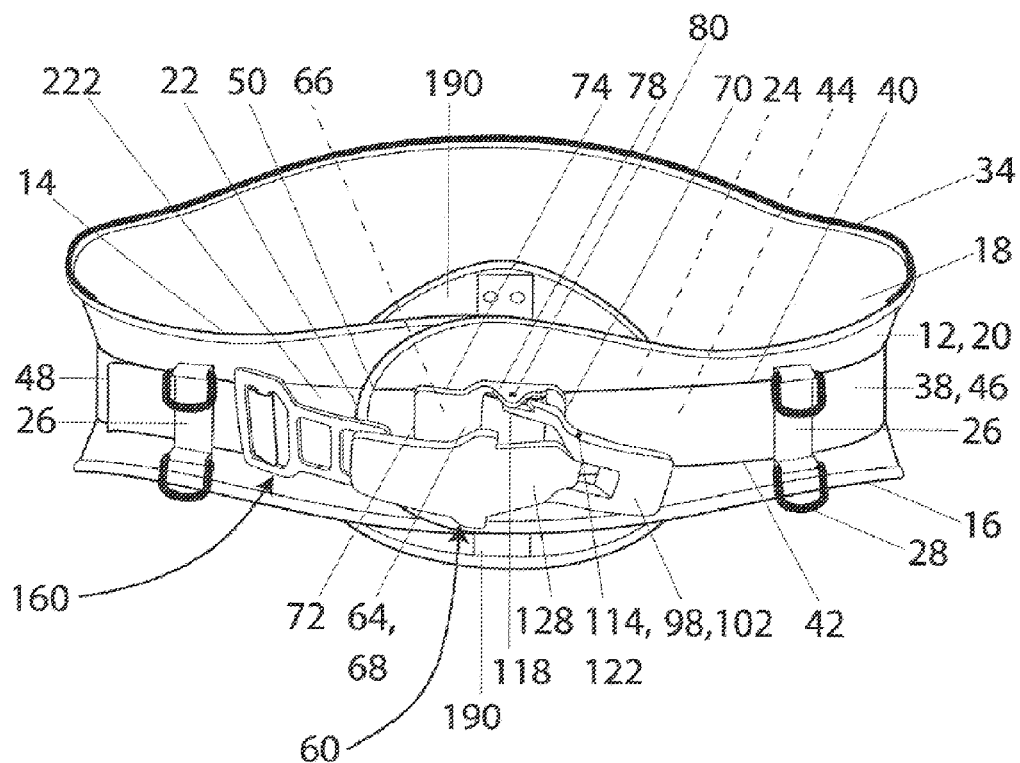
FIG. 3 is a front orthographic view of a first belt including a separating zipper, a second belt, a buckle, an adjustable belt glide, and an abdominal support brace.
Figure 12:
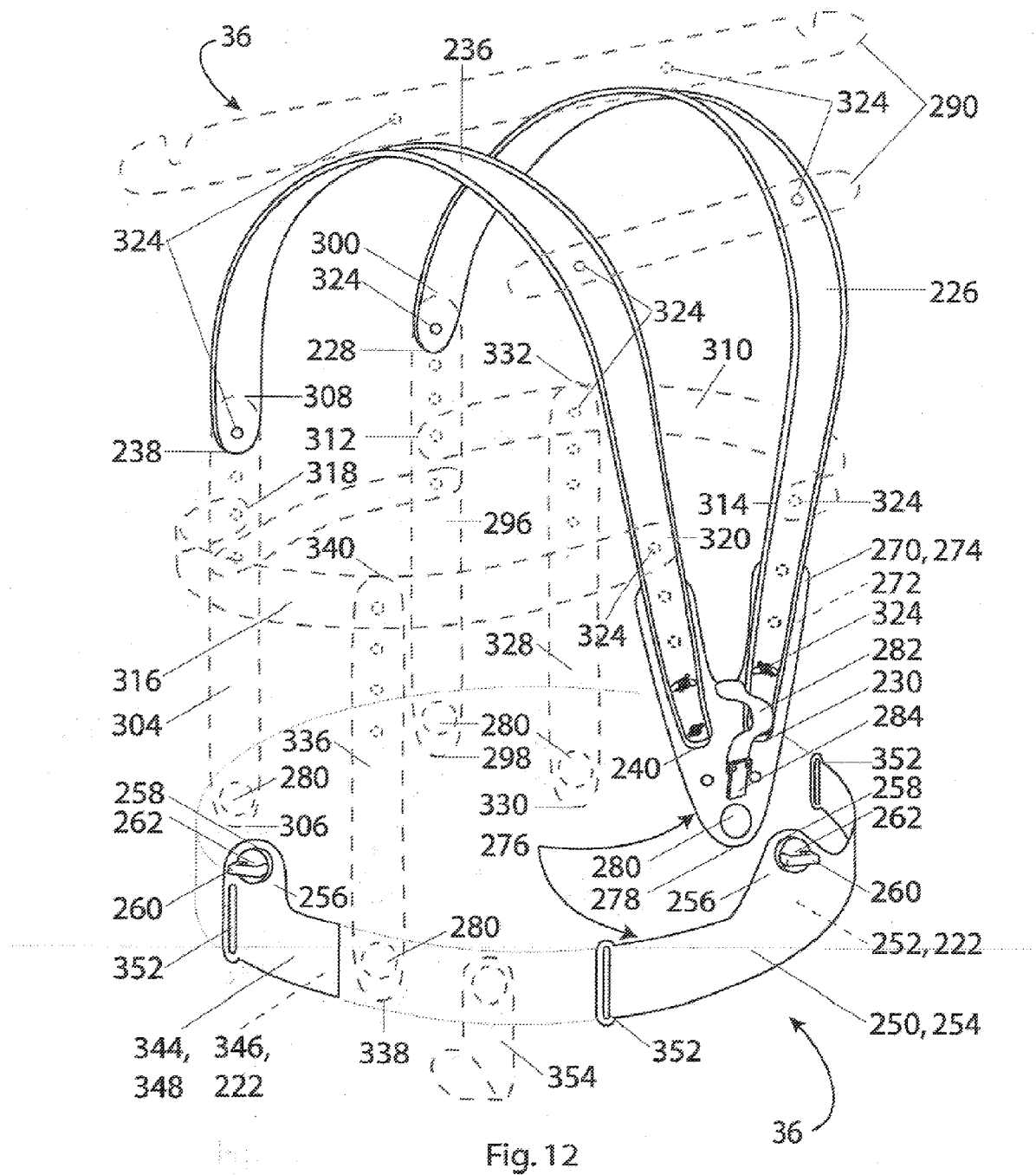
FIG. 12 is an orthographic view showing two shoulder supports, shoulder supports attachment means, two yoke supports, two front vertical supports, two side vertical supports and two side horizontal supports, one load bearing hook and attachment means.
Figure 13:
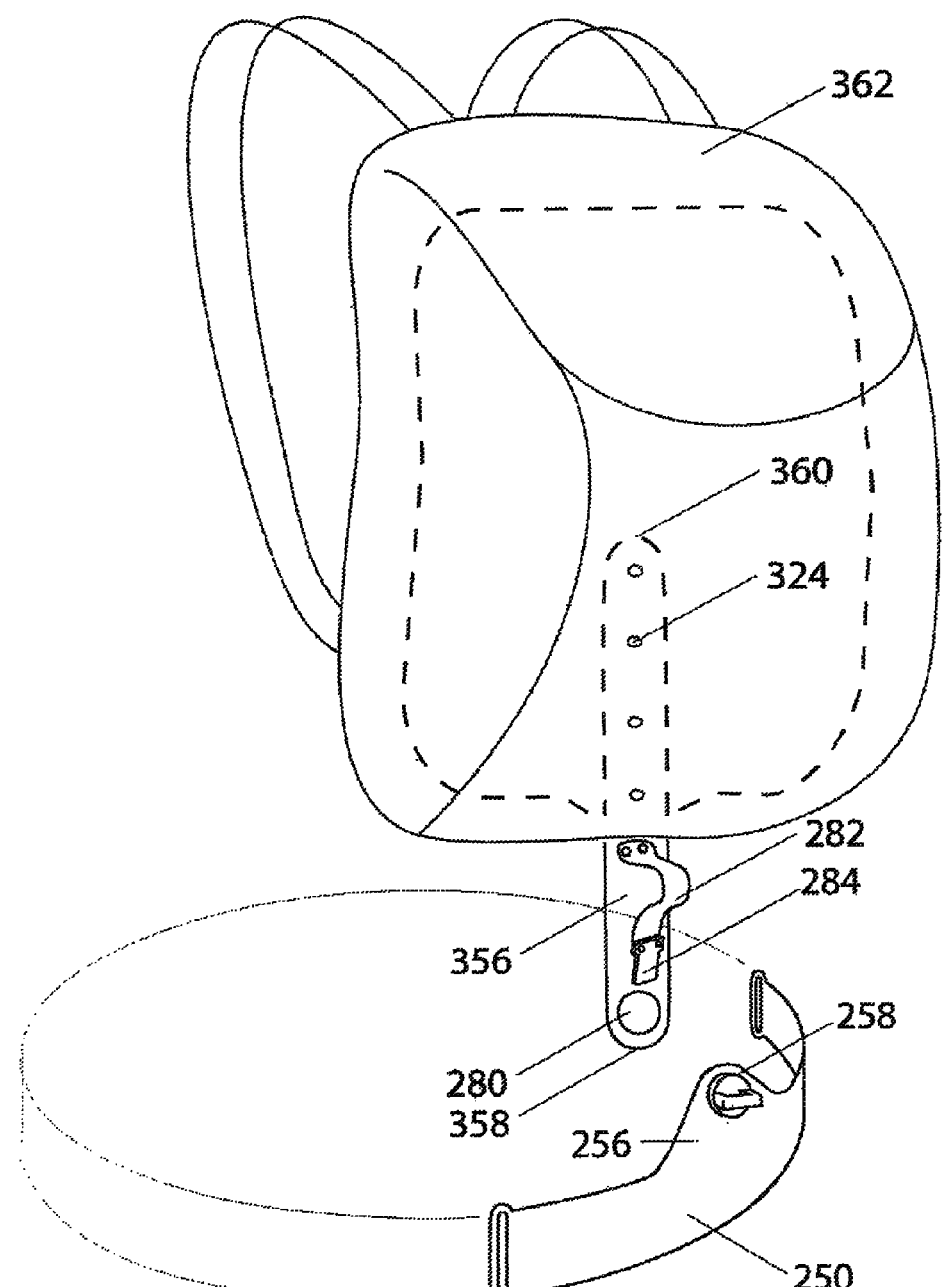
FIG. 13 is an orthographic view showing a vertical back support, attachment means and a load.

The first belt 12, as shown in FIGS. 1-3, has an upper edge 14 with a zipper interface 34, a lower edge 16, inner surface 18, an outer surface 20, a first end 22, a second end 245 and a plurality of loops 26. As an optional addition, a plurality of D-rings 28, as best shown in FIG. 3, can be included to increase the functionally of the first belt 12. Also, at least one belt hook 354 can be attached to the first belt 12. The belt hook(s) 354, as shown in FIG. 12, are utilized to provide support for a load that is hung from the hook. As also shown in FIGS. 1-3, the first belt 12 is contoured to a human body by the combination of three shapes.

As shown in FIGS. 1-3, the second belt 38 also has an upper edge 40, a lower edge 42, an inner surface 44, an outer surface 46, a first end 48 and a second end 50. The first belt 12 and the second belt 38 function in combination to provide a unitary support around a person's waist. The first end 48 of the second belt 38 is sequentially inserted through each of the plurality of loops 26 on the first belt 12 and follows the circumference of the first belt 12. Both the first belt 12 and the second belt 38 are made of a material selected from but not limited to the group consisting of breathable cotton, cotton/polypropylene duck fabric, wool flannel, nylon, polypropylene mesh fabric, cotton, polypropylene, nylon webbing, molded rubber, space age polymers, and other fireproof or waterproof materials.

Figure 4:
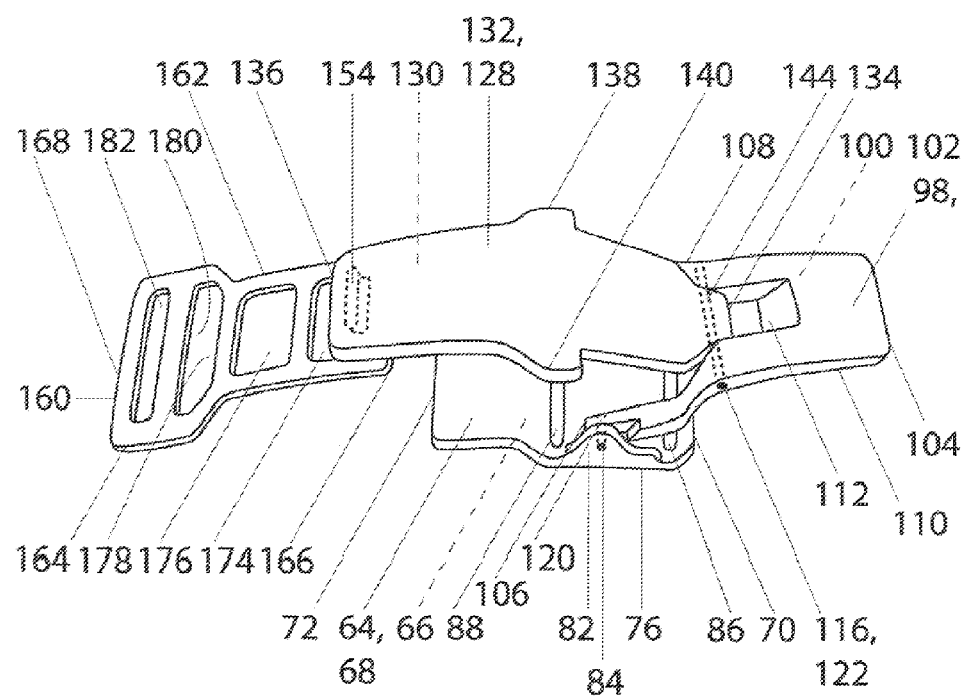
FIG. 4 is a front orthographic view of the buckle and the adjustable belt glide.
Figure 5:
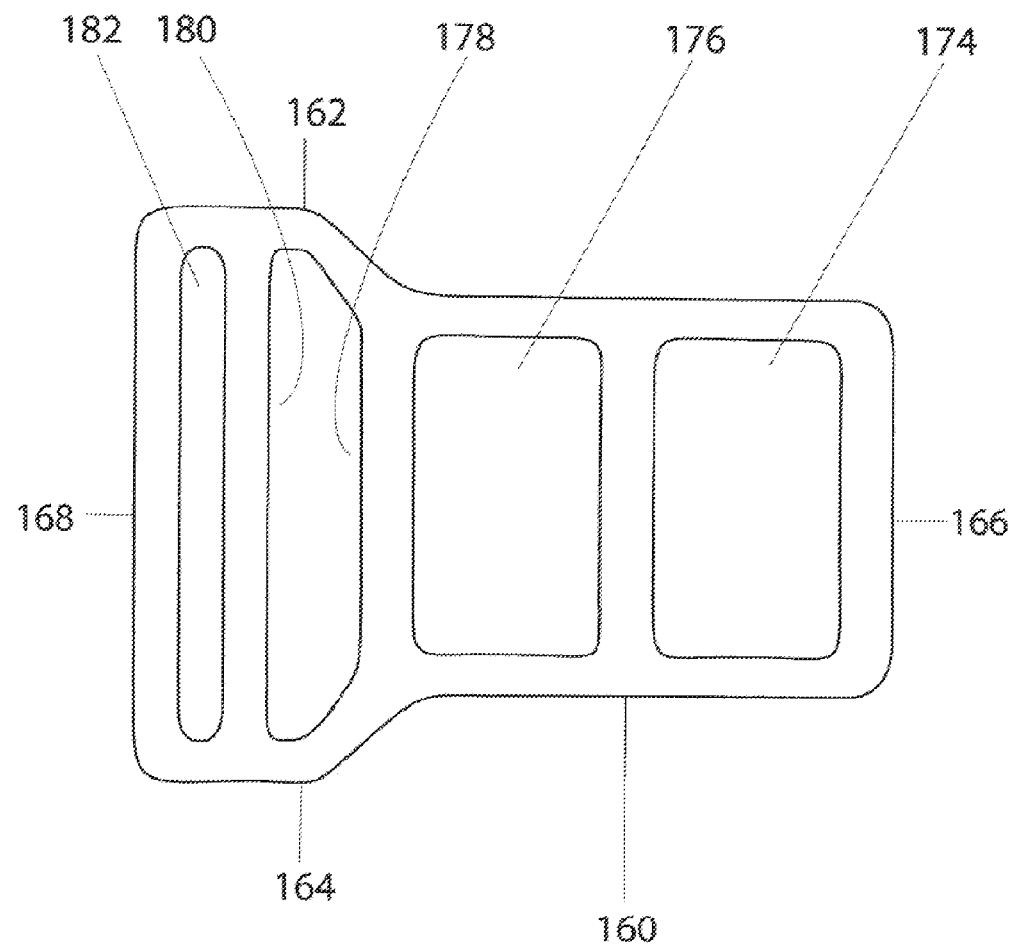
FIG. 5 is a front elevational view of the adjustable belt glide.

As shown in FIGS. 1, 3, 4, the buckle 60 is attached to the second end 50 of the second belt 38 and is comprised of a base section 64, a first articulated section 98 and a second articulated section 128. As shown best in FIG. 3, the base section 64 has an inner surface 66, an outer surface 68, a right edge 70, a left edge 72, an upper edge 74 and a lower edge 76. Extending upward from the upper edge 74 is a first vertical tab 78 having a first bore 80 adjacent the first tab's upper edge, and extending upward from the lower edge 76 is a second vertical tab 82 having a second bore 84 adjacent the second tab's upper edge. Located adjacent the base's right edge 70 is a right belt opening 86, and located adjacent the base's left edge 72 is a left belt opening 88. The first end 48 of the second belt 38 is sequentially inserted through the second and first belt openings 88,86, and when the first end 48 of the second belt 38 is pulled tight, the buckle 60 is securely attached to the second end 50 of the second belt 38.

The buckle 60 utilizes a lever action which allows the buckle 60 to be mechanically cinched snuggly for support or instantly released by a single action. The buckle, interfacing with the adjustable belt glide 160 is adjustable to six sizes to provide comfortable securement for individuals having a larger girth after a meal or to accommodate the layering of clothing.

The first articulated section 98, as also shown in FIGS. 3 and 4, has an inner surface 100, an outer surface 102, a right edge 104, a left edge 106, an upper edge 108, and a lower edge 110. From the left edge 106 is a centered slot 112 that extends inward substantially two-thirds the length of the articulated section 98. Located substantially at the center of the upper edge 108 is a third bore 114, and located substantially at the center of the lower edge 110 is a fourth bore 116. Located adjacent the left edge 106 on the upper edge 108 is a fifth bore 118 that is in alignment with the first bore 80 on the base section 64, and located adjacent the left edge 106 on the lower edge 110 is a sixth bore 120 that is in alignment with the second bore 84 on the base section 64.

The second articulated section 128, as also shown in FIGS. 3 and 4, has an inner surface 130, an outer surface 132, a right edge 134, a left edge 136, an upper edge 138, and a lower edge 140. Located adjacent the right edge 134 on the upper edge 138 is a seventh bore 144 that extends through the second articulated section from the upper edge 138 to the lower edge 140. The second articulated section 128 pivots outward from and is attached to the first articulated section 98 by a pin 122 that is inserted through the third bore 114 on the first section 98 and into and through the seventh bore 144 on the second section 128 and on the through the fourth bore 116 on the first articulated section 98. The first articulated section 98 and the second articulated section 128 are dimensioned to allow the buckle 60 to be placed in a substantially flat planar position which allows the buckle 60 to be unobtrusive when worn by a person. Extending inward from a location adjacent the second articulated section's left edge inner surface 130 is an interface tab 154.

The adjustable belt glide 160, as shown in FIGS. 1, 3, 4, 5, is utilized for the buckle and the belt, and has an upper edge 162, a lower edge 164, a right edge 166, a left edge 168, a first tab opening 174, a second tab opening 176, a third tab opening 178, a first belt opening 180 and a second belt opening 182. It should be noted that the third tab opening 178 and the first belt opening 180 together function as a combination tab/belt opening. The first end 48 of the second belt 38 is sequentially inserted through the first and second belt openings 180,182, and when the first end 48 of the second belt 38 is pulled tight, the adjustable belt glide 160 is securely attached to the second belt 38. The interface tab 154 on the second articulated section 128 is selectively inserted inward through the first, second or third tab opening 174,176, 178 thereby securely connecting the buckle 60 to the adjustable belt glide 160, and since the buckle 60 is attached to the second end 50 of the second belt 38, and the adjustable belt glide 160 is attached to the first end 48 of the second belt 38, the two respective ends of the second belt 38 are maintained together, which also maintains the first belt 12 in a circular orientation that is utilized when the two belts 12,38 are worn around a person's mid-section. The buckle 60 and the adjustable belt glide 160 are made of polypropylene, nylon, a space age polymer, steel, aluminum or carbon fiber.

With the adjustable buckle 60, the belt glide 160 is six-way adjustable, with the third tab opening 178 adaptable for use with both the belt and/or the buckle tab. The belt can be inserted through the opening 180 and the buckle's interface tab 154 can also be inserted into and clipped onto the combination opening. Where the buckle tab is placed on the belt glide depends on the desire, support requirement and/or size of the person who is wearing the LBSS 10.

It should be noted that while three tab openings 174,176, 178 and two belt openings 180,182 are disclosed, additional tab openings and/or belt openings can be included. The additional openings allow the belts 12,38 to be secured together for instant additional abdominal area and lower back support or fitting around a larger circumference waist, which is necessary after a large meal, or when layering more clothing underneath.

The optional abdominal support brace 190, as shown in FIGS. 3, 6, 9 and 10, has a perimeter edge 192, an inner surface 194 and an outer surface 196.

Figure 6:
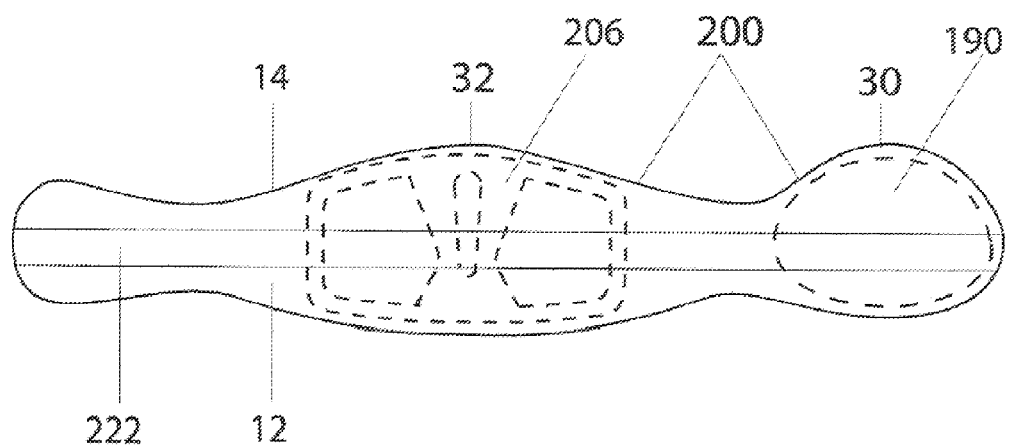
FIG. 6 is a front elevational view of the first belt showing the inserted locations of the abdominal support brace and the back support brace, and a structure that encloses and provides a means for attaching the brace(s).
Figure 7:
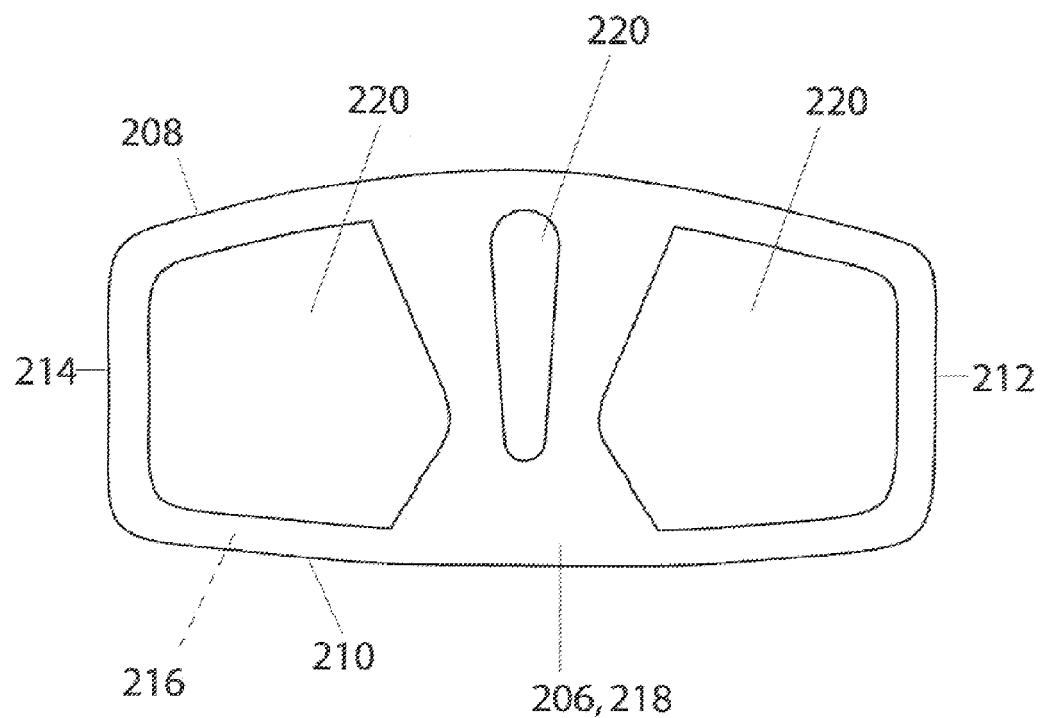
FIG. 7 is a front elevational view of a back support brace.
Figure 8:
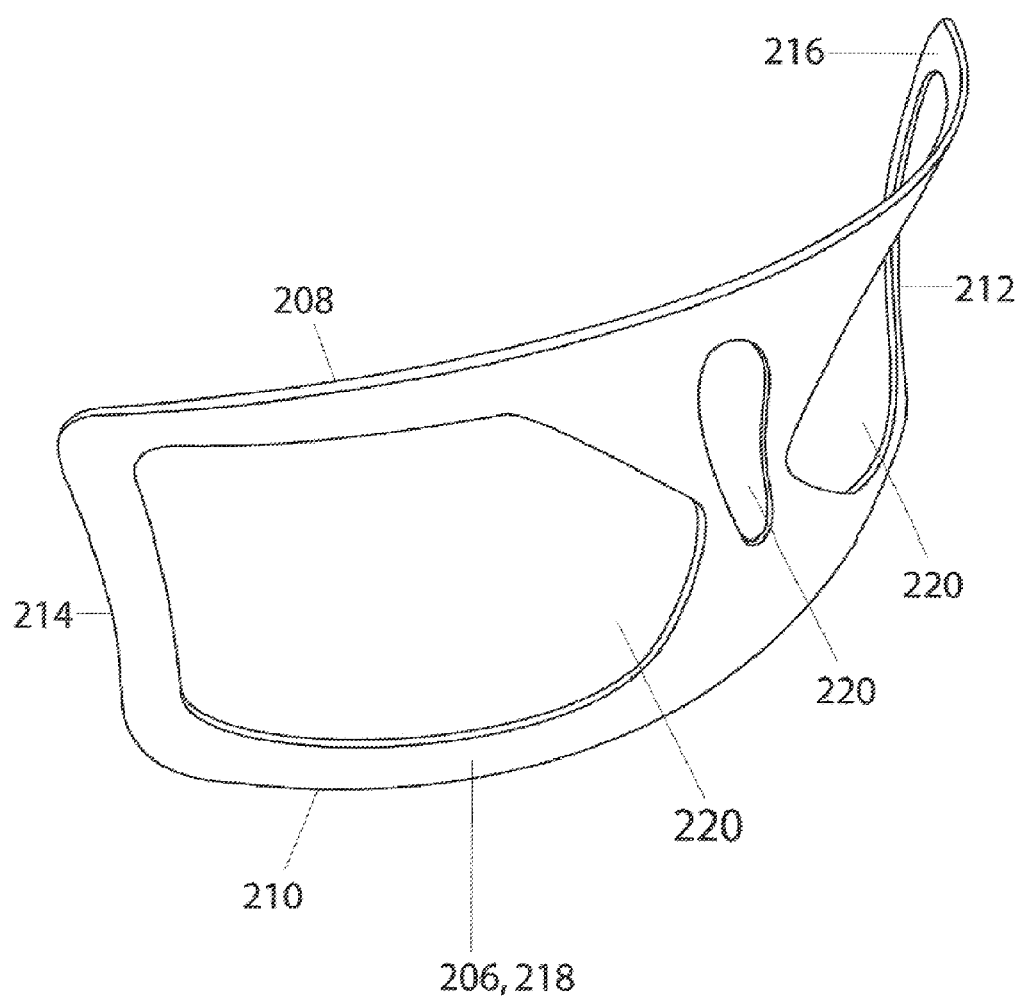
FIG. 8 is an orthographic view of the back support brace with three cut-outs.
Figure 9:
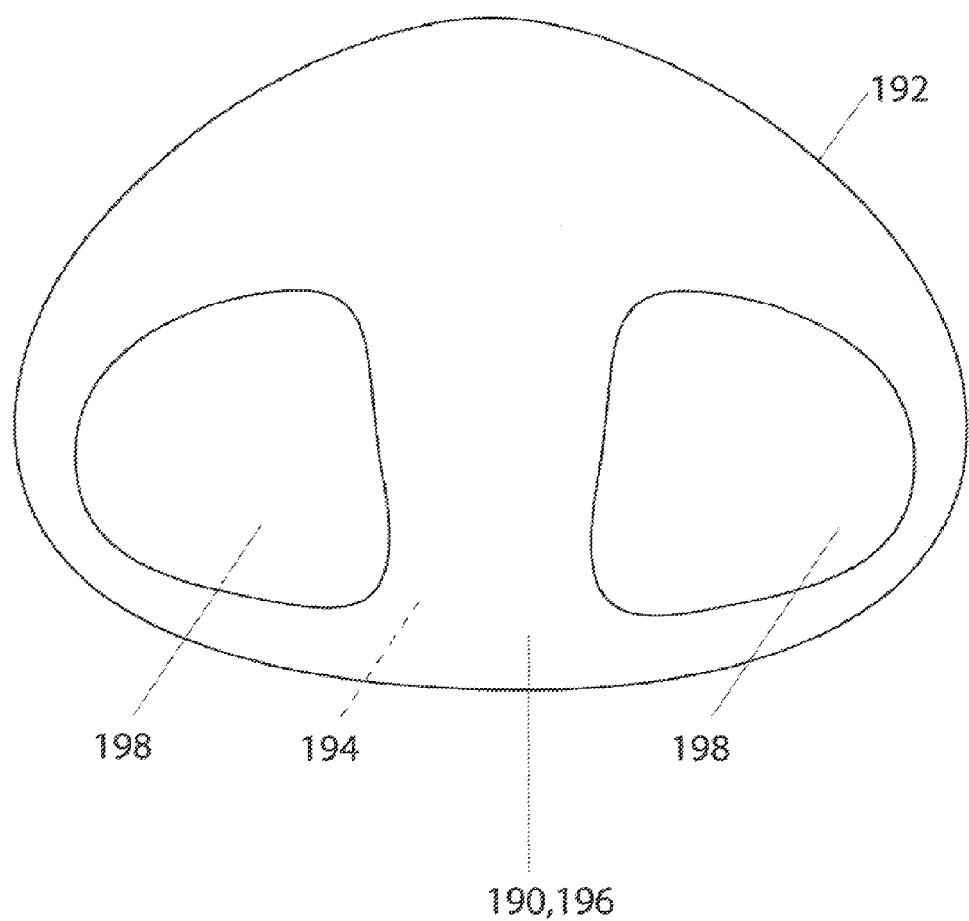
FIG. 9 is a front elevational view of the abdominal support brace with two cut-outs.

Attached by an attachment means 200 to the rear of the first belt 12 is the back support brace 206, as shown in FIGS. 6, 7 and 8, which has an upper edge 208, a lower edge 210, a right edge 212, a left edge 214, an inner surface 216 and an outer surface 218. It is important to note that the back support brace 206 is specialty designed to provide support by following the physiology of a typical person's back, as shown in FIGS. 2, 6,7, 8 and 11. Both the abdominal support brace 190 and the back support brace 206 can include at least one cut-out 198,220 to provide ventilation and to reduce the weight of each respective support brace 190,206. The cut-outs 198,220 can be variable size depending on the desire of the user and the particular application of the LBSS 10.

Both the abdominal support brace 190 and the back support brace 206 are made of polypropylene, nylon, wood, metal, molded rubber or space age polymers. The attachment means 200 for attaching the abdominal support brace 190 and the back support brace 206 is comprised of two pockets 30,32 that are located on the top edge 14 of the first belt 12, as shown in FIG. 6. Each pocket 30,32 allows the respective support brace to be inserted into or removed from the first belt 12.

Figure 10:
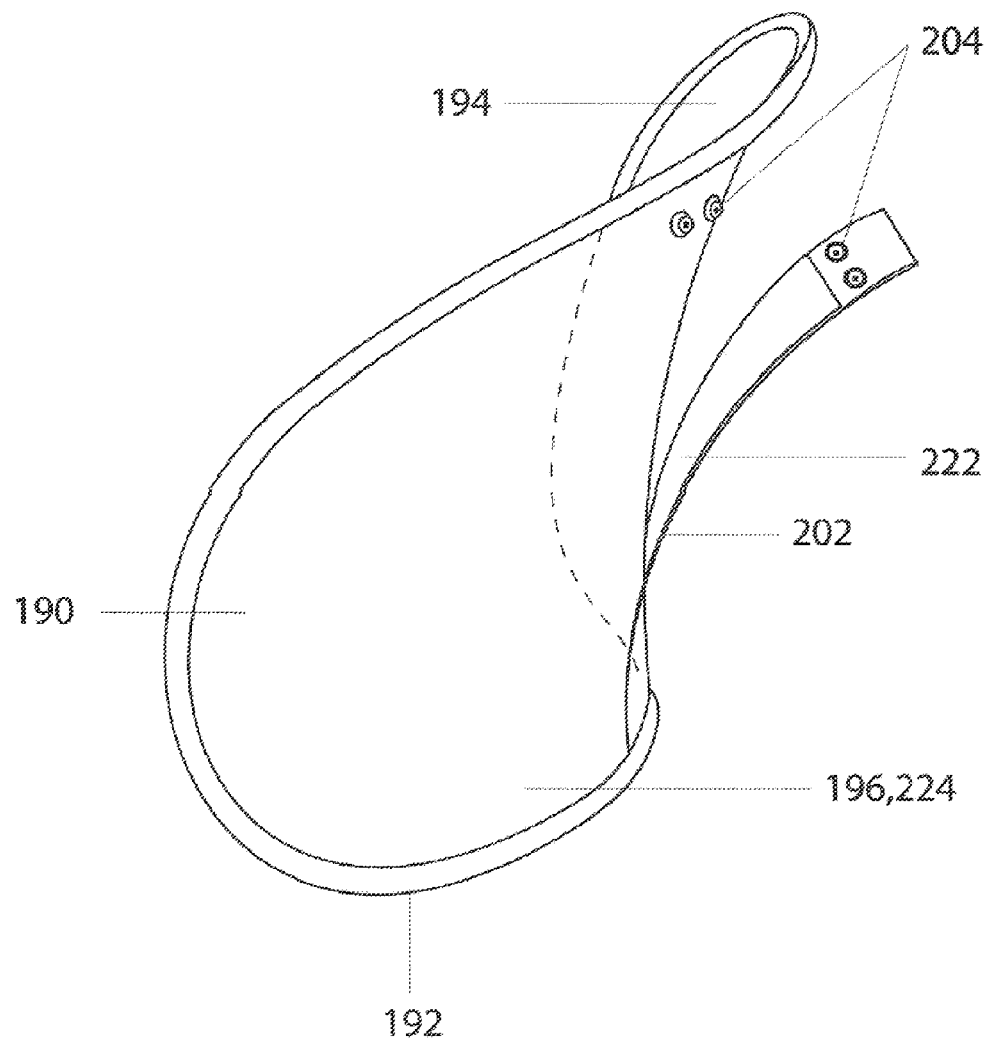
FIG. 10 is an orthographic view of an abdominal support brace.
Figure 11:
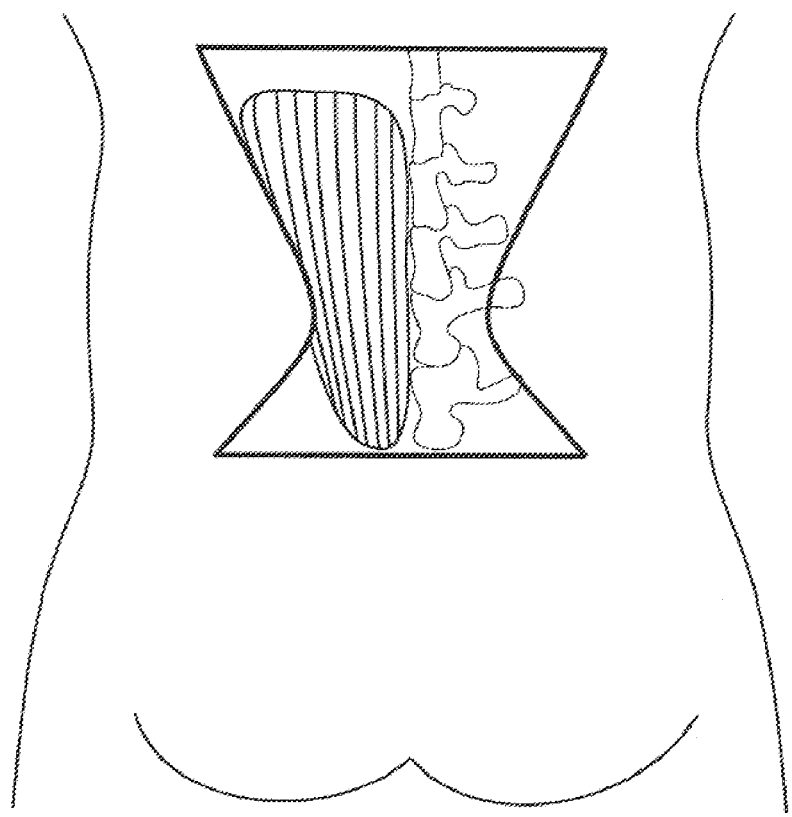
FIG. 11 is a cut-out view showing how the back support brace is designed to provide maximum support to a person's lower back physiology.

The braces 190,206 can also be attached by use of a cover 224 that encloses each brace. The cover, as shown in FIGS. 3 and 10, includes at least one strap 202 that extends upward from a lower edge of the cover. Located at an upper edge of the strap 202 is an attachment means 204 that allows the strap(s) and the cover with enclosed brace to be removably secured to the first belt 12 at a desired location. The attachment means for securing the strap can include a snap closure 204, a hook and loop fastener 222, or any other similar removable attachments means. As best shown in FIGS. 3 and 10, the cover with enclosed brace is placed behind the belt 12 and the strap 202 is pulled up in front of the belt 12, but behind belt 38, thereby positioning the cover with the hook and loop, and then the upper edge of the strap is attached, thereby securing the cover with the brace enclosed.

Additionally, the two support braces 190,206 can also be attached to the first belt 12 by a hook and loop 222 and fastener 204 or can be molded in or sewn in each respective pocket.

As shown in FIG. 12, the first shoulder support 226 has a first end 228 and a second end 230, and the second shoulder support 236 also has a first end 238 and a second end 240.

The first ends 228,238 of both the first shoulder support 226 and the second shoulder support 236 terminate at a person's upper chest, and the second ends 230,240 are attached by an attachment means to the second belt 38. Both shoulder supports 226,236 can be telescoping in order to facilitate the use of the LBSS 10 by people of various sizes and heights. Additionally, a bracket (not shown) or hooks(s) can be attached to either or both shoulder supports to provide an anchor for supporting a load.

As shown in FIG. 12, the attachment means 276 for attaching the shoulder supports 226,236 to the second belt 38 is comprised of a support base belt anchor 250 having an inner surface 252 and an outer surface 254 and that is located on the second belt 38, and a V-shaped shoulder support base 270 having an inner surface 272 and an outer surface 274. Attached by an attachment means 324 to each of the V's upward-extending sections is the second end 230,240 of one of each of the shoulder supports. Adjacent the lower point 278 of the V-shaped shoulder support base 270 is a bore 280, and located adjacent an upward-extending section 256 of the support base belt anchor 250 is a connector base 258 with an outward-extending tab 260 having an opening 262 therethrough that is dimensioned to interface with the bore 280 on the V-shaped shoulder support base 270. Extending from the shoulder support base 270 is a flexible strip 282 with a tab 284 on the end. The strip's tab 284 is dimensioned to be inserted into the opening 262 on the outward-extending tab 260. The bore 280 on the shoulder support base 270 interfaces with the outward-extending tab 260 extending from the connector base 258 such that the opening 262 on the tab 260 is accessible through the bore 280, and the tab 284 at the end of the flexible strip 282 is then inserted into and frictionally held through the opening 262, thereby securing the V-shaped shoulder support base to the support base belt anchor. Both the connector base 258 on the support base belt anchor 250 and the bore 280 on the V-shaped shoulder support base 270 are circular, as shown in FIG. 12. The circular shape allows the attached shoulder supports 226, 236, as well as any object(s) that is being carried/worn on a person's back, to pivot side to side, which significantly increases the comfort, support, and balance of a person when participating in a variety of activities while carrying/wearing the object(s). In lieu of the tab 284 and opening 262, a spring detent (not shown) or other similar attachment means can also be utilized.

Additionally, as shown in FIG. 12, the two front vertical supports 296,304 can be attached to the second belt 38 by a flexible strip with a tab on the end that is inserted into a corresponding opening that is located on the second belt 38 or by a spring detent. These attachment means are similar to the attachment means utilized for the two shoulder supports 226,236 as previously disclosed. As with the shoulder supports, the two front vertical supports 296,304 can pivot side to side which increases the comfort and balance of a person when participating in a variety of activities' while carrying/wearing an object(s).

In an alternate design confirmation (not shown) the connector base 258 and outward-extending tab 260 can be located adjacent the lower point 278 on the V-shaped shoulder support base 270. The bore that the connector base 258 is inserted through is located on the upward-extending section 256 on the support base belt anchor 250. The attachment method is the same as the first design and can be used on any/or all vertical supports.

To add further utility and strength to the shoulder supports 226,236, several additional supports, which are all shown in FIG. 12, can also be utilized. At least one yoke support 290, is located adjacent a person's shoulders and is attached by an attachment means 324 horizontally to the first shoulder support 226 and the second shoulder support 236.

A first front vertical support 296 having a first end 298 and a second end 300. The first end 298 is attached by an attachment means 344 to the second belt 38, and the second end 300 is attached by an attachment means 324 to the first end 228 of the first shoulder support 226. The first front vertical support 296 provides additional securement and support of the first shoulder support 226 along the front section of a person's torso.

A second front vertical 304 support having a first end 306 and a second end 308. The first end 306 is attached by an attachment means 344 to the second belt 38 and the second end 308 is attached by an attachment means 324 to the first end 238 of the second shoulder support 236. The second front vertical support 304 provides additional securement and support of the second shoulder support 236 along the front of a person's torso.

A first side horizontal support 310 having a first end 312 and a second end 314. The first end 312 is attached by an attachment means 324 to the first front vertical support 296, and the second end 314 is attached by an attachment means 324 to the first shoulder support 226. The first side horizontal support 310 provides front to back securement of the first front vertical support 296 to the first shoulder support 226.

A second side horizontal support 316 having a first end 318 and a second end 320, wherein the first end is attached by an attachment means 324 to the second front vertical support 304, and the second end 320 is attached by an attachment means 324 to the second shoulder support 236. The second horizontal support 316 provides front to back securement to the second front vertical support 304 to the second shoulder support 236.

A first side vertical support 328 having a first end 330 and a second end 332, wherein the second end 332 is attached by an attachment means 324 to the first side horizontal support 310, and the first end 330 is attached by an attachment means 344 to the second belt 38. The first side vertical support 328 provides additional securement and support along the right side of a person's torso, adjacent a person's kidney.

A second side vertical support 336 having a first end 338 and a second end 340, wherein the second end 340 is attached by an attachment means 324 to the second side horizontal support 316, and the first end 338 is attached by an attachment means 344 to the second belt 38. The second side vertical support 336 provides additional securement and support along the left side of a person's torso, adjacent a person's kidney. Located on the second end of all the vertical supports 296,304,328,336 are multiple bores for fasteners, which creates an attachment means with multiple positions to accommodate varying heights of users.

The attachment means for attaching the first front vertical support, the second front vertical support, the first side vertical support and the second side vertical support to the second belt further comprises a vertical support belt anchor 344 having an inner surface 346 and an outer surface 348, wherein the verticals support belt anchor is attached to the second belt and the first end of a respective vertical support is secured to the vertical support belt anchor by use of a bore on the first end that interfaces with a corresponding connector base 258 having an outward-extending tab 260 and an opening 262, and that is located on the outer surface of the vertical support belt anchor 344.

The attachment means 324 for attaching the first shoulder support, the second shoulder support, the yoke support(s), the first front vertical support, the second front vertical support, the first side horizontal support and the second side horizontal support is selected from the group consisting of a rivet, a nut and bolt combination, a spring detent (not shown) or the like.

Additionally, as shown in FIG. 12, the support belt base anchor 250 and the vertical support belt anchor 344 can include at least one belt opening 352. Each belt opening 352 allows the second belt 38 to be inserted through the opening 352 to provide secure attachment of each anchor to the belt, which in turn secures the respective vertical support that is attached to the anchor.

In order to provide increased comfort when wearing the LBSS, any of the horizontal and/or vertical supports can utilize a pad (not shown) that is placed between the support and a person's body where the support could make contact. The pad can be made of a fabric material, a lightweight composite material, foam or other similar resilient material, and is thick enough to provide the necessary comfort without interfering with the functionality of the back rack 36 when connected to the LBSS 10.

While the invention has been described in detail and pictorially shown in the accompanying drawings it is not to be limited to such details, since many changes and modification may be made to the invention without departing from the spirit and the scope thereof. Hence, it is described to cover any and all modifications and forms which may come within the language and scope of the claims.

The invention claimed is:

1. A lower back support system (LBSS) that provides increased support to a person's lower spine/muscle groups said LBSS comprising a first belt, a second belt, a quick release lever action buckle, an adjustable belt glide, an abdominal support brace, a back support brace, a first shoulder support having a first end and a second end, and a second shoulder support having a first end and a second end, wherein said lever action buckle and said adjustable belt glide allow said first belt and said second belt to be securely maintained around a person's waist at a selective tightness, wherein substantially centered and attached by an attachment means to said first belt is said abdominal support brace, and substantially centered and enclosed in a pocket, that is formed by an inner lining and an outer fabric that is located at said first belt is said back support brace, wherein from said second belt, configured to extend upward along a person's back and continuing over the person's right shoulder, is said first shoulder support, and configured to extend from said second belt upward along a person's back and over the person's left shoulder is said second shoulder support, wherein both shoulder supports are attached by an attachment means to said second belt and both shoulder supports configured to terminate at a location on a person's upper chest, wherein the attachment means for attaching said shoulder supports to said second belt is comprised of a support base belt anchor that is located on said second belt, and a shoulder support base, wherein attached by an attachment means to said shoulder support base is the second end of one of each of said shoulder supports, wherein adjacent a lower point of said shoulder support base is a bore, and located adjacent an upward-extending section of said support base belt anchor is a connector base with an outward-extending tab having an opening therethrough that is dimensioned to interface with the bore on said shoulder support base, wherein extending from the shoulder support base is a flexible strip with a tab on the end, wherein the strip's tab is dimensioned to be inserted into the opening on the outward-extending tab, and frictionally held within the opening, thereby securing said shoulder support base to said support base belt anchor, wherein when said shoulder support base is secured to said support base belt anchor, a load that is worn with said LBSS is allowed to pivot from side to side as a person walks or runs, whereby when wearing said LBSS, the use of said first and second belts with said abdominal support brace and said back support brace, or the use of said belts with said abdominal support brace and said back support brace along with said first and second shoulder supports provides support, against a strain a person experiences when lifting, carrying or wearing a load, wherein the weight of the load is shifted off a person's shoulders and spine to their hips and legs, thereby removing the load on the person's spine and entirely transferring the load to the person's hips and legs.

2. The LBSS as specified in claim 1 wherein said abdominal support brace and back support brace are contoured to match the physiology of a person's abdominal area and lower back.

3. The LBSS as specified in claim 1 wherein said means for attaching said abdominal support brace and said back support brace is comprised of two pockets located on an inner surface of said first belt, wherein each pocket allows said respective abdominal support brace and said back support brace to be inserted into or removed from said first belt.

4. The LBSS as specified in claim 1 wherein said attachment means for attaching said abdominal support brace and said back support brace is selected from the group consisting of at least one webbing strap, hook and loop fasteners and snaps.

* * * * *